United States Patent

Yano et al.

(10) Patent No.: US 6,717,002 B2
(45) Date of Patent: Apr. 6, 2004

(54) METHOD OF PRODUCING STEROID DERIVATIVES

(75) Inventors: Shingo Yano, Kawagoe (JP); Ryutaro Yamagami, Hannou (JP); Kenji Nozaki, Hannou (JP); Tetsuji Asao, Tokorozawa (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 222 days.

(21) Appl. No.: 09/926,349

(22) PCT Filed: Feb. 16, 2001

(86) PCT No.: PCT/JP01/01119

§ 371 (c)(1),
(2), (4) Date: Oct. 18, 2001

(87) PCT Pub. No.: WO01/60836

PCT Pub. Date: Aug. 23, 2001

(65) Prior Publication Data

US 2002/0143199 A1 Oct. 3, 2002

(30) Foreign Application Priority Data

Feb. 18, 2000 (JP) .......................................... 2000-40927

(51) Int. Cl.[7] .................................................. C07J 75/00
(52) U.S. Cl. ....................................... 552/530; 530/615
(58) Field of Search ................................. 552/530, 615

(56) References Cited

U.S. PATENT DOCUMENTS

2001/0039269 A1 * 11/2001 Peters et al. ................ 514/177

OTHER PUBLICATIONS

P. N. Rao, et al., Steroids, vol. 59, pp. 621–627, XP–002939737, "Preparative Chemical Methods for Aromatization of 19–nor–Δ4–3–OXOSTEROIDS", Nov. 1994.
J. March, Reactions, pp. 529–532, XP–002229124, "Advanced Organic Chemistry", 1985.

* cited by examiner

*Primary Examiner*—Brenda Coleman
(74) *Attorney, Agent, or Firm*—Oblon, Spivak, McClelland, Maier & Neustad, P.C.

(57) ABSTRACT

A method of producing 3-alkoxy-1,3,5(10)-triene-6-one-steroid derivatives having, in the steroid skeleton thereof, a partial structure of A- and B-rings represented by formula (2):

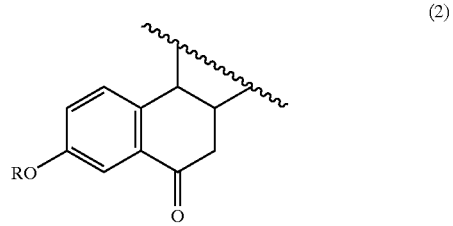

(wherein R represents an alkyl group, a cycloalkyl group, an alkenyl group, or an aralkyl group), including reacting a 19-norsteroid derivative having, in the steroid skeleton thereof, a partial structure of A- and B-rings represented by formula (1):

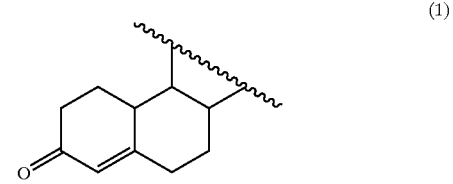

with an alcohol represented by ROH (wherein R has the same meaning as defined above) and iodine in the absence of a rare earth compound catalyst. According to the method of the present invention, 3-alkoxy-1,3,5(10)-triene-6-one-steroids can be selectively produced from 19-norsteroides through a single reaction step without employment of a special catalyst.

3 Claims, No Drawings

METHOD OF PRODUCING STEROID DERIVATIVES

This application is a national stage entry under 35 U.S.C. § 371 of PCT/JP01/01119, filed Feb. 16, 2001.

TECHNICAL FIELD

The present invention relates to a method of selectively producing 3-alkoxy-1,3,5(10)-triene-6-one-steroid derivatives, which are useful for drugs and diagnostic agents.

BACKGROUND ART

Conventionally, there has been disclosed, in *Steroids*, 59, 621 (1994), a method for producing 3-alkoxy-1,3,5(10)-triene-6-one-steroid derivatives (hereinafter referred to as 3-alkoxytriene steroids) having, in the steroid skeleton thereof, a partial structure of A- and B-rings represented by formula (2):

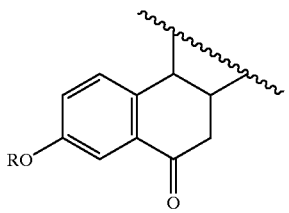

(wherein R represents an alkyl group, a cycloalkyl group, an alkenyl group, or an aralkyl group) from 19-norsteroid derivatives (hereinafter referred to as 19-norsteroids) having, in the steroid skeleton thereof, a partial structure of A- and B-rings represented by formula (1):

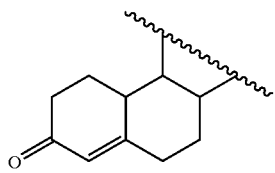

by the reaction, in methanol, of 19-nor-4-androstene-3,17-dione with iodine in the presence of ceric ammonium nitrate as a rare earth compound catalyst, to thereby yield estrone-methyl ether (predominant product) and oxoestrone-methyl ether (by-product) in the form of a mixture. However, this method is not industrially efficient, since it involves a reaction employing a rare earth metal compound catalyst which requires burdensome waste treatment; the yield of 6-one species is as low as 23–27%; and high-cost silica gel column chromatography must be carried out so as to separate from by-product and purify the target compound.

As stated above, the conventional technique is not preferred as a method for industrially producing 3-alkoxytriene-6-one steroids from 19-norsteroids.

Accordingly, an object of the present invention is to provide a method for industrially producing 3-alkoxytriene-6-one steroids from 19-norsteroids in a simple manner, with high efficiency and high safety, at low costs, and employing neither a special apparatus nor a reagent raises problems in terms of waste treatment.

DISCLOSURE OF THE INVENTION

The present inventors have carried out extensive studies, and quite unexpectedly, have found that when 19-norsteroid is reacted with alcohol and iodine in the absence of a rare earth compound, which may serve as an oxidizing agent, a 6-oxo species can be obtained selectively, as contrasted to the case of the presence of a rare earth compound catalyst, whereby the aforementioned 6-desoxo species is predominantly produced. The present invention has been accomplished on the basis of this finding.

Accordingly, the present invention provides a method of producing 3-alkoxy-1,3,5(10)-triene-6-one-steroid derivatives having, in the steroid skeleton thereof, a partial structure of A- and B-rings represented by formula (2):

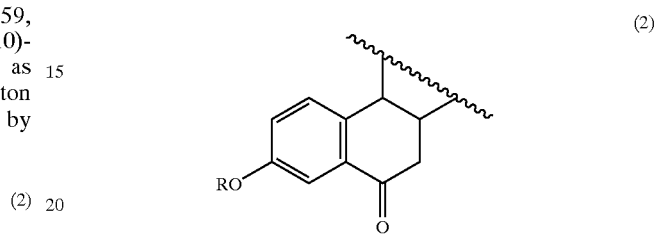

(wherein R represents an alkyl group, a cycloalkyl group, an alkenyl group, or an aralkyl group), comprising reacting a 19-norsteroid derivative having, in the steroid skeleton thereof, a partial structure of A- and B-rings represented by formula (1):

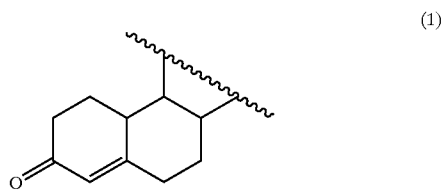

with an alcohol represented by ROH (wherein R has the same meaning as defined above) and iodine in the absence of a rare earth compound catalyst.

BEST MODE FOR CARRYING OUT THE INVENTION

The production method of the present invention is represented by the following reaction scheme:

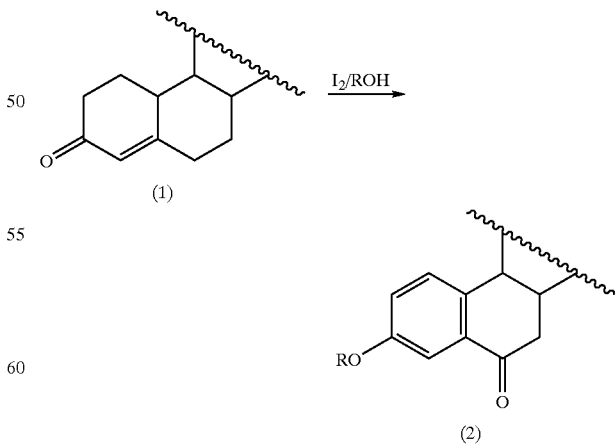

(wherein R has the same meaning as defined above).

In the present invention, any 3-oxo-4-ene-19-norsteroids having, in the steroid skeleton thereof, a partial structure of A- and B-rings represented by the above formula (1) may be employed as a starting material. They may be of natural origin, semi-synthesized, or synthesized. These 19-norsteroids may have any number of substituent at any position of the rings constituting the steroid skeleton (represented by the below-described structure of formula (3)), so long as the substituent or the position of substitution does not affect the reaction according to the present invention. Examples of the position of substitution which does not affect the reaction according to the present invention include 11-, 12-, 15-, 16-, and 17-positions.

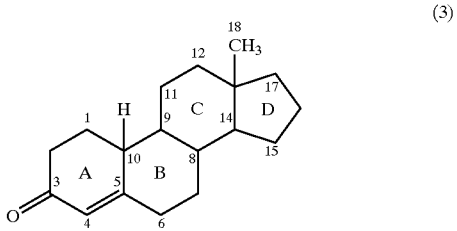

(3)

Examples of the substituent which does not affect the reaction according to the present invention include halogen atoms (e.g., fluorine, chlorine, bromine, iodine), a hydroxyl group, acyloxy groups having a total carbon number of 2 to 7, optionally substituted alkyl groups having a total carbon number of 1 to 10, optionally substituted acyl groups having have a total carbon number of 1 to 7, optionally substituted aralkyl groups having a carbon number of 7 to 11, alkenyl groups having a carbon number of 2 to 4, alkynyl groups having a carbon number of 2 to 4, and optionally substituted alkylidene groups having a carbon number of 1 to 4.

Examples of the acyloxy groups having a carbon number of 2 to 7 include an acetyloxy group, a propionyloxy group, a butylyloxy group, an isobutylyloxy group, an isovaleryloxy group, a pivaloyloxy group, and a heptanoyloxy group.

Examples of the alkyl groups having a carbon number of 1 to 10 include a methyl group, an ethyl group, a propyl group, an isopropyl group, a butyl group, an isobutyl group, a t-butyl group, a pentyl group, a 4-isopropylpentyl group, a hexyl group, a heptyl group, an octyl group, a nonyl group, and a decyl group. These alkyl groups may have a substituent. Examples of the substituent include halogen atoms, a hydroxyl group, a hydroxycarbonyl group, alkoxy groups having a carbon number of 1 to 4 (e.g., methoxy, ethoxy, propoxy, isopropoxy, butoxy, isobutoxy), acyl groups having a total carbon number of 1 to 5 (e.g., formyl, acetyl, propionyl, butylyl, isobutylyl, isovaleryl, pivaloyl), aryloxy groups having a carbon number of 6 to 10 (e.g., phenoxy, naphthyloxy) which may have 1–3 substituents. Examples of the substituents of the aryloxy groups having a carbon number of 6 to 10 and optionally having 1–3 substituents include halogen atoms, a hydroxyl group, alkyl groups having a carbon number of 1 to 4 (e.g., methyl, ethyl, propyl, isopropyl, butyl, isobutyl, t-butyl), alkoxy groups having a carbon number of 1 to 4 (e.g., methoxy, ethoxy, propoxy, isopropoxy, butoxy), dialkylamino groups having a total carbon number of 2 to 6 (e.g., dimethylamino, diethylamino, dipropylamino, diisopropylamino), acyl groups having a total carbon number of 1 to 4 (e.g., formyl, acetyl, propionyl, butylyl), alkoxyalkyl groups having a total carbon number of 2 to 6 (e.g., methoxymethyl, methoxyethyl, methoxypropyl, ethoxyethyl, isopropoxyethyl, ethoxybutyl), dialkylaminocarbonyl groups having a total carbon number of 3 to 9 (e.g., dimethylaminocarbonyl, diethylaminocarbonyl, dipropylaminocarbonyl, dibutylaminocarbonyl), and dialkylaminoalkyl groups having a total carbon number of 3 to 9 (e.g., dimethylaminomethyl, dimethylaminoethyl, dimethylaminopropyl, diethylaminomethyl, diethylaminoethyl, diethylaminopropyl, diisopropylaminomethyl, dibutylaminomethyl).

Examples of the acyl groups having a total carbon number of 1 to 7 include a formyl group, an acetyl group, a propionyl group, a butylyl group, an isobutylyl group, an isovaleryl group, a pivaloyl group, and a heptanoyl group. The substituents which may be incorporated into these acyl groups include the aforementioned examples of the substituents of the optionally substituted alkyl groups.

Examples of the aralkyl groups having a carbon number of 7 to 11 include a benzyl group, a phenetyl group, a phenylpropyl group, and a naphthylmethyl group. The substituents which may be incorporated into these aralkyl groups include the aforementioned examples of the substituents of the optionally substituted alkyl groups.

Examples of the alkenyl groups having a carbon number of 2 to 4 include a vinyl group, an allyl group, an isopropenyl group, and a 2-butenyl group. Examples of the alkynyl groups having a carbon number of 2 to 4 include an ethynyl group, a 2-propynyl group, and 2-butynyl group.

Examples of the alkylidene groups having a carbon number of 1 to 4 include a methylidene group, an ethylidene group, and a propylidene group. The substituents which may be incorporated into these alkylidene groups include the aforementioned examples of the substituents of the optionally substituted alkyl groups as well as alkoxycarbonyl groups having a total carbon number of 2 to 7 (e.g., methoxycarbonyl, ethoxycarbonyl, propoxycarbonyl, butoxycarbonyl).

Examples of alcohols represented by ROH include linear or branched lower alcohols having a carbon number of 1 to 6, cycloalkanol having a carbon number of 3 to 6, allyl alcohol, and benzyl alcohol. Examples of the linear or branched lower alcohols having a carbon number of 1 to 6 include methanol, ethanol, n-propanol, isopropanol, n-butanol, sec-butanol, t-butanol, pentanol, and hexanol. Examples of the cycloalkanol having a carbon number of 3 to 6 include cyclopropanol, cyclobutanol, cyclopentanol, and cyclohexanol. Of these, methanol, ethanol, n-propanol, isopropanol, allyl alcohol, and benzyl alcohol are preferably employed for the reaction of the present invention, with methanol, ethanol, propanol and isopropanol being more preferred.

In the method of the present invention, 19-norsteroid (1) is caused to react with iodine and alcohol (ROH) in an appropriate solvent and in the absence of a rare earth compound catalyst.

No particular limitation is imposed on the appropriate solvent, and any solvent can be used so long as it does not affect the reaction. Examples of the solvent include hydrocarbons such as benzene, toluene, and xylene; aprotic polar solvents such as acetonitrile and N,N-dimethylformamide; and ethers such as dimethoxyethane, tetrahydrofuran, and dioxane, with acetonitrile being preferred. Alcohols represented by ROH may also be used in the reaction of the present invention.

The reaction according to the present invention proceeds in the presence of oxygen, and the oxygen dissolved in the reaction mixture may suffice for this purpose. However, in order to promote the reaction on an industrial scale and enhance yield and selectivity of the target compound, additional oxygen may be supplied to the reaction mixture. Specifically, oxygen-containing gas such as air or oxygen gas is introduced into the reaction mixture. The air which is to be introduced is preferably dried by being passed through a desiccant such as calcium chloride, potassium hydroxide, sodium hydroxide, or concentrated sulfuric acid. Although the rate and time of feeding oxygen gas or air vary in accordance with conditions such as the amount of fed 19-norsteroid (1), the type and amount of solvent, and reaction temperature, the rate of feeding is preferably 1–10,000 mL/min/L, more preferably 10–8,000 mL/min/L, further more preferably 10–5,000 mL/min/L, particularly preferably 10–3,000 mL/min/L, and the time of feeding, which may vary in accordance with the rate of feeding, is preferably 0.1–8 hours, more preferably 0.5–4 hours, further more preferably 0.5–2 hours.

Iodine is preferably used in an amount of 1–8 equivalents by mol based on 19-norsteroid (1), more preferably 1–6 equivalents by mol, further more preferably 2–5 equivalents by mol. The alcohol represented by ROH is preferably used in an amount of 5–10,000 equivalents by mol based on 19-norsteroid (1), more preferably 50–1,000 equivalents by mol. The reaction temperature is preferably −30° C. to 150° C., more preferably −30° C. to 120° C., further more preferably −20° C. to a temperature at which the solvent is refluxed. The reaction time for advantageously proceeding the reaction is preferably 0.1–24 hours, more preferably 0.5–12 hours, further more preferably 1–6 hours. In a particularly preferred mode, the reaction is carried out at −20° C. to 30° C. concomitant with passage of oxygen or air in an initial stage and, subsequently at 50–90° C., although the conditions may vary in accordance with the type of alcohol (ROH) employed.

The 3-alkoxytriene steroid (2) obtained through the method of the present invention may be isolated and purified through any of generally known isolation-purification methods such as recrystallization and silica gel chromatography.

EXAMPLES

The method of the present invention will next be described in detail by way of examples.

Referential Example 1

Synthesis of Ethyl (E)-19-norpregna-4,17(20)-diene-3-one-21-oate

To a solution of ethyl diethylphosphonoacetate (179 g, 0.8 mol) in THF (600 mL), a 20% solution (286 g) of sodium ethoxide (0.84 mol) in ethanol and 3-ethoxyestra-3,5-dien-17-one (60.0 g, 0.2 mol) were sequentially added at room temperature. The resultant mixture was heated to 75° C. and stirred for 14 hours. The reaction mixture was cooled to room temperature, and 6N hydrochloric acid (200 mL) and water (300 mL) were added to the mixture. The resultant mixture was further stirred for 20 minutes. The mixture was extracted with ethyl acetate, and the organic phase was washed sequentially with an aqueous solution of sodium bicarbonate and saturated brine. The washed matter was dried over magnesium sulfate anhydrate, filtered, and evaporated under reduced pressure. The formed precipitates were recrystallized from diisopropyl ether, to thereby yield 55.3 g of the title compound (yield 81%).

Melting point: 130–131° C.

MS (EI): 342 (M+)

$^1$H-NMR (CDCl$_3$) δ: 0.89 (3H, s, 18-CH$_3$), 1.28 (3H, t, J=7.3 Hz, 21-OCH$_2$CH$_3$), 4.15 (2H, q, J=7.3 Hz, 21-OCH$_2$CH$_3$), 5.55 (1H, t, J=2.7 Hz, 20-CH), 5.85 (1H, s, 4-CH) ppm.

Example 1

Synthesis of 6-oxoestrone-3-methyl Ether

Iodine (7.61 g, 30 mmol) and 19-nor-4-androstene-3,17-dione (2.72 g, 10 mmol) were dissolved in a mixture of acetonitrile (75 mL) and methanol (75 mL), to thereby form a reaction mixture. The reaction mixture was stirred for two hours while oxygen was introduced (50 mL/min) thereto under cooling in an ice-bath. The resultant mixture was maintained at room temperature, and after stirring of the mixture for a further 1.5 hours, introduction of oxygen was stopped and the mixture was refluxed for one hour. The reaction mixture was cooled to room temperature, and an aqueous solution of sodium thiosulfate was added to the mixture. The mixture was extracted with chloroform, and the organic phase was washed sequentially with an aqueous solution of sodium bicarbonate and saturated brine. The washed matter was dried over magnesium sulfate anhydrate, filtered, and evaporated under reduced pressure. The formed precipitates were recrystallized from acetone, to thereby yield 2.17 g of the title compound (yield 73%). The remaining mother liquor was purified through silica gel column chromatography (chloroform), to thereby further obtain 0.35 g of the title compound (overall yield: 85%).

Melting point: 143–145° C.

MS (EI): 298 (M+)

$^1$H-NMR (CDCl$_3$) δ: 0.92 (3H, s, 18-CH$_3$), 3.85 (3H, s, 3-OCH$_3$), 7.12 (1H, dd, J=8.8, 2.9 Hz, 2-CH), 7.34 (1H, d, J=8.8 Hz, 1-CH), 7.57 (1H, d, J=2.9 Hz, 4-CH) ppm.

Example 2

Synthesis of 6-oxoestrone-3-ethyl Ether

Iodine (3.81 g, 15 mmol) and 19-nor-4-androstene-3,17-dione (1.36 g, 5 mmol) were dissolved in a mixture of acetonitrile (37.5 mL) and ethanol (37.5 mL), to thereby form a reaction mixture. The reaction mixture was stirred for two hours while air which had been dried by passing through a calcium chloride tube was introduced (50 mL/min) thereto under cooling in an ice-bath. The resultant mixture was maintained at room temperature, and after stirring of the mixture for a further 1.5 hours, introduction of air was stopped and the mixture was refluxed for one hour. The reaction mixture was cooled to room temperature, and an aqueous solution of sodium thiosulfate was added to the mixture. The mixture was extracted with chloroform, and the organic phase was washed sequentially with an aqueous solution of sodium bicarbonate and saturated brine. The washed matter was dried over magnesium sulfate anhydrate, filtered, and evaporated under reduced pressure. The formed precipitates were recrystallized from an ethanol-hexane mixed solvent, to thereby yield 1.1 g of the title compound (yield 70%).

Melting point: 161–163° C.

MS (EI): 312 (M+)

$^1$H-NMR (CDCl$_3$) δ: 0.92 (3H, s, 18-CH$_3$), 1.42 (3H, t, J=7.1 Hz, 3-OCH$_2$CH$_3$), 4.08 (2H, q, J=7.1 Hz, 3-OCH$_2$CH$_3$), 7.12 (1H, dd, J=8.6, 2.9 Hz, 2-CH), 7.35 (1H, d, J=8.6 Hz, 1-CH), 7.56 (1H, d, J=2.9 Hz, 4-CH) ppm.

Example 3

Synthesis of 6-oxoestrone-isopropyl Ether

Iodine (7.61 g, 30 mmol) and 19-nor-4-androstene-3,17-dione (2.72 g, 10 mmol) were dissolved in a mixture of acetonitrile (75 mL) and isopropanol (75 mL), to thereby form a reaction mixture. The reaction mixture was stirred for two hours while oxygen was introduced (50 mL/min) thereto under cooling in an ice-bath. The resultant mixture was maintained at room temperature, and after stirring of the mixture for a further 1.5 hours, introduction of oxygen was stopped and the mixture was refluxed for one hour. The reaction mixture was cooled to room temperature, and an aqueous solution of sodium thiosulfate was added to the mixture. The mixture was extracted with chloroform, and the organic phase was washed sequentially with an aqueous solution of sodium bicarbonate and saturated brine. The washed matter was dried over magnesium sulfate anhydrate, filtered, and evaporated under reduced pressure. The formed precipitates were recrystallized from acetone, to thereby yield 1.3 g of the title compound (yield 40%). The remaining mother liquor was purified through silica gel column chromatography (chloroform), to thereby further obtain 1.3 g of the title compound (overall yield: 80%).

Melting point: 159–162° C.

MS (EI): 326 (M+)

$^1$H-NMR(CDCl$_3$) δ: 0.92 (3H, s, 18-CH$_3$), 1.33 (3H, d, J=5.9 Hz, 3-OCH(C$\underline{H}_3$)$_2$, 1.34 (3H, d, J=5.9 Hz, 3-OCH(C$\underline{H}_3$)$_2$, 4.63 (1H, m, 3-OC$\underline{H}$(CH$_3$)$_2$, 7.09 (1H, dd, J=8.6, 3.0 Hz, 2-CH), 7.33 (1H, d, J=8.6 Hz, 1-CH), 7.57 (1H, d, J=3.0 Hz, 4-CH) ppm.

Example 4

Synthesis of 6-oxoestradiol-3-methyl Ether

Iodine (7.61 g, 30 mmol) and 19-nortestosterone (2.74 g, 10 mmol) were dissolved in a mixture of acetonitrile (75 mL) and methanol (75 mL), to thereby form a reaction mixture. The reaction mixture was stirred for two hours while oxygen was introduced (50 mL/min) thereto under cooling in an ice-bath. The resultant mixture was maintained at room temperature, and after stirring of the mixture for a further 1.5 hours, introduction of oxygen was stopped and the mixture was refluxed for one hour. The reaction mixture was cooled to room temperature, and an aqueous solution of sodium thiosulfate was added to the mixture. The mixture was extracted with chloroform, and the organic phase was washed sequentially with an aqueous solution of sodium bicarbonate and saturated brine. The washed matter was dried over magnesium sulfate anhydrate, filtered, and evaporated under reduced pressure. The formed precipitates were recrystallized from methanol, to thereby yield 590 mg of the title compound (yield 20%). The remaining mother liquor was purified through silica gel column chromatography (chloroform), to thereby further obtain 1.41 g of the title compound (overall yield: 67%).

Melting point: 77–84° C.

MS (EI): 300 (M+)

$^1$H-NMR (CDCl$_3$) δ: 0.79 (3H, s, 18-CH$_3$), 3.76 (1H, t, J=8.5 Hz, 17-CH), 3.84 (3H, s, 3-OCH$_3$), 7.11 (1H, dd, J=8.8, 2.9 Hz, 2-CH), 7.35 (1H, d, J=8.8 Hz, 1-CH), 7.56 (1H, d, J=2.9 Hz, 4-CH) ppm.

Example 5

Synthesis of 6-oxoestrone-methyl Ether

Iodine (508 mg, 2 mmol) and 19-nor-4-androstene-3,17-dione (272 mg, 1 mmol) were dissolved in a mixture of acetonitrile (12 mL) and methanol (3 mL), to thereby form a reaction mixture. The reaction mixture was stirred for two hours while oxygen was introduced (50 mL/min) thereto under cooling in an ice-bath. The resultant mixture was maintained at room temperature, and after stirring of the mixture for a further 1.5 hours, introduction of oxygen was stopped and the mixture was refluxed for one hour. The reaction mixture was cooled to room temperature, and an aqueous solution of sodium thiosulfate was added to the mixture. The mixture was extracted with chloroform, and the organic phase was washed sequentially with an aqueous solution of sodium bicarbonate and saturated brine. The washed matter was dried over magnesium sulfate anhydrate, filtered, and evaporated under reduced pressure. The residue was purified through silica gel column chromatography (chloroform), to thereby yield 230 mg of the title compound (yield: 77%).

Example 6

Synthesis of 6-oxoestrone-methyl Ether

Iodine (560 mg, 2.2 mmol) and 19-nor-4-androstene-3,17-dione (200 mg, 0.735 mmol) were dissolved in methanol (10 mL), and the resultant mixture was stirred for two hours under cooling in an ice-bath. The mixture was maintained at room temperature, and the mixture was further stirred for 1.5 hours, and subsequently refluxed for one hour. The reaction mixture was cooled to room temperature, and an aqueous solution of sodium thiosulfate was added to the mixture. The mixture was extracted with chloroform, and the organic phase was washed sequentially with an aqueous solution of sodium bicarbonate and saturated brine. The washed matter was dried over magnesium sulfate anhydrate, filtered, and evaporated under reduced pressure. The residue was purified through silica gel column chromatography (chloroform), to thereby yield 177 mg of the title compound (yield: 81%).

Example 7

Synthesis of 6-oxoestrone-methyl Ether

Iodine (1.27 g, 5 mmol) and 19-nor-4-androstene-3,17-dione (272 mg, 1 mmol) were dissolved in methanol (15 mL), and the resultant mixture was stirred for two hours under cooling in an ice-bath. The temperature of the mixture was maintained at room temperature, and the mixture was further stirred for 1.5 hours, and subsequently, refluxed for one hour. The reaction mixture was cooled to room temperature, and an aqueous solution of sodium thiosulfate was added to the mixture. The mixture was extracted with chloroform, and the organic phase was washed sequentially with an aqueous solution of sodium bicarbonate and saturated brine. The washed matter was dried over magnesium sulfate anhydrate, filtered, and evaporated under reduced pressure. The residue was purified through silica gel column chromatography (chloroform), to thereby yield 220 mg of the title compound (yield: 74%).

Example 8

Synthesis of ethyl(E)-3-ethoxy-19-norpregna-1,3,5 (10), 17(20)-tetraene-6-one-21-oate Ethyl (E)-19-norpregna-4,17(20)-diene-3-one-21-oate (2.00 g, 5.85 mmol) obtained in Referential Example 1 was dissolved in ethanol (100 mL), and iodine (3.26 g, 12.8 mmol) was added to the solution. The resultant reaction mixture was stirred for one hour while air which had been dried by passing through a calcium chloride tube was introduced (50 mL/min) thereto under cooling in an ice-bath. The resultant mixture was maintained at room emperature, and after stirring of the mixture for a further one hour, introduction of air was stopped and the mixture was refluxed for one hour. The reaction mixture was cooled to room temperature, and an aqueous solution of sodium hydrogensulfite was added to the mixture. The mixture was stirred for 30 minutes and concentrated under reduced pressure. The formed precipitates were washed with water and collected through filtration. The collected solid was washed by ethanol with heating, to thereby yield 1.54 g of the title compound (yield 69%).

Melting point: 135–136° C.

MS (EI): 382 (M+)

$^1$H-NMR (CDCl$_3$) δ: 0.88 (3H, s, 18-CH$_3$), 1.30 (3H, t, J=7.1 Hz, 20-OCH$_2$CH$_3$), 1.42 (3H, t, J=7.1 Hz, 3-OCH$_2$CH$_3$), 4.08 (2H, q, J=7.1 Hz, 3-OCH$_2$CH$_3$), 4.17 (2H, q, J=7.1 Hz, 20-OCH$_2$CH$_3$), 5.61 (1H, t, J=2.4 Hz, 20-CH), 7.11 (1H, dd, J=8.6, 3.0 Hz, 2-CH), 7.34 (1H, d, J=8.6 Hz, 1-CH), 7.55 (1H, d, J=3.0 Hz, 4-CH) ppm.

Elementary analysis: as C$_{24}$H$_{30}$O$_4$; Calculated (%): C, 75.36; H, 7.91; Found (%): C, 75.40; H, 7.99.

Comparative Example 1

Synthesis of 6-oxoestrone-methyl Ether by Use of a Rare Earth Compound Catalyst

Iodine (7.01 g, 27.6 mmol), 19-nor-4-androstene-3,17-dione (5.00 g, 18.4 mmol), and ceric ammonium nitrate (15.1 g, 27.6 mmol) were dissolved in methanol (150 mL), and the resultant mixture was refluxed for two hours. The resultant reaction mixture was cooled to room temperature, and an aqueous solution of sodium thiosulfate was added to the mixture. The mixture was extracted with chloroform, and the organic phase was washed sequentially with an aqueous solution of sodium bicarbonate and saturated brine. The washed matter was dried over magnesium sulfate anhydrate, filtered, and evaporated under reduced pressure. The residue was subjected to a separation-purification step through silica gel column chromatography (chloroform), to thereby yield 2.20 g of the title compound (yield: 40%) and, as a by-product, 2.45 g of estrone-methyl ether (yield: 47%).

Comparative Example 2

Necessity of Iodine

In a mixture of acetonitrile (3.5 mL) and methanol (3.5 mL), 19-nor-4-androstene-3,17-dione (136 mg, 0.5 mmol) was dissolved. The resultant mixture was stirred for one hour while air which had been dried by passing through a calcium chloride tube was introduced thereto at room temperature. Subsequently, introduction of air was stopped and the mixture was refluxed for one hour. The reaction mixture was cooled to room temperature, and an aqueous solution of sodium thiosulfate was added to the mixture. The resultant mixture was extracted with ethyl acetate, and the organic phase was washed sequentially with an aqueous solution of sodium bicarbonate and saturated brine. The washed matter was dried over magnesium sulfate anhydrate, filtered, and evaporated under reduced pressure, ending up with recovery of starting materials.

INDUSTRIAL APPLICABILITY

According to the method of the present invention, 3-alkoxy-1,3,5(10)-triene-6-one-steroids can be selectively produced from 19-norsteroides through a single reaction step without employment of a special catalyst.

What is claimed is:

1. A method of producing 3-alkoxy-1,3,5(10)-triene-6-one-steroid derivatives having, in the steroid skeleton thereof, a partial structure of A- and B-rings represented by formula (2):

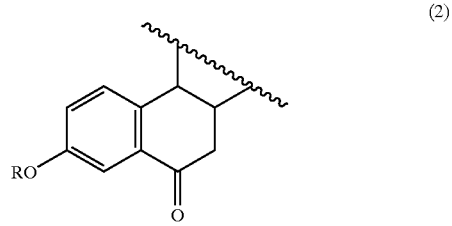

(2)

(wherein R represents an alkyl group, a cycloalkyl group, an alkenyl group, or an aralkyl group), comprising reacting a 19-norsteroid derivative having, in the steroid skeleton thereof, a partial structure of A- and B-rings represented by formula (1):

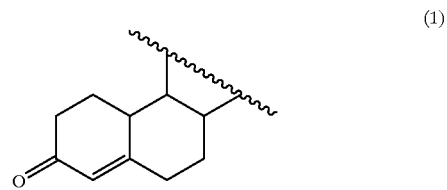

(1)

with an alcohol represented by ROH (wherein R has the same meaning as defined above) and iodine in the absence of a rare earth compound catalyst.

2. The method according to claim 1, wherein the reaction is carried out in the presence of oxygen.

3. The method according to claim 1 or 2, wherein the alcohol represented by ROH is a lower alcohol having a carbon number of 1 to 6, a cycloalkanol having a carbon number of 3 to 6, a alkenol having a carbon number of 2 to 4, or an aralkyl alcohol having a carbon number of 7 to 10.

* * * * *